United States Patent [19]
Jallat et al.

[11] Patent Number: 5,814,716
[45] Date of Patent: Sep. 29, 1998

[54] CELL LINES FROM A TRANSGENIC MOUSE WHICH EXPRESS BIOLOGICALLY ACTIVE IX FACTOR

[75] Inventors: Sophie Jallat, Strasbourg; Pierre Meulien, Paris; Andréa Pavirani; Frédéric Perraud, both of Strasbourg, all of France

[73] Assignee: Transgene S.A., Courbevoie, France

[21] Appl. No.: 394,210

[22] Filed: Feb. 24, 1995

Related U.S. Application Data

[63] Continuation of Ser. No. 38,085, Mar. 29, 1993, abandoned, which is a continuation of Ser. No. 675,889, filed as PCT/FR90/00606 Aug. 9, 1990, published as WO91/02056 Feb. 21, 1991, abandoned.

[30] Foreign Application Priority Data

Aug. 9, 1989 [FR] France ................................. 89 10720

[51] Int. Cl.$^6$ .............................. C12N 5/00; C12N 15/00; C12P 21/04
[52] U.S. Cl. ......................... 800/2; 435/69.6; 435/240.1; 435/71.3; 935/60
[58] Field of Search ............................. 800/2; 435/69.6, 435/71.3, 240.2; 935/60

[56] References Cited

FOREIGN PATENT DOCUMENTS

| | | |
|---|---|---|
| 167420 | 1/1986 | European Pat. Off. . |
| 0298807 | 1/1989 | European Pat. Off. . |
| 298807 | 1/1989 | European Pat. Off. . |
| 307248 | 3/1989 | European Pat. Off. . |
| 316558 | 5/1989 | European Pat. Off. . |
| 223755 | 4/1990 | United Kingdom . |

OTHER PUBLICATIONS

K.H. Choo et al, "Expression of Active Human Blood Clotting Factor IX in Transgenic Mice: Use of a cDNA with Complete mRNA Sequence," Nucleic Acids Research, vol. 15, No. 3, 1987 (Oxford, GB) pp. 871–884.

D.S. Anson et al, "The Gene Structure of Human Anti–haemophilic Factor IX," The EMBO Journal, vol. 3, No. 5, 1984, IRL Press Ltd., (Oxford, GB), pp. 1053–1060.

P.H. Reitsma et al, "The Putative Factor IX Gene Promoter in Hemophilia B leyden," Blood, vol. 72, No. 3, Sep. 1988, Grune & Stratton, Inc., (New York, US); pp. 1074–1076 see abstract; p. 1074, col. 2; p. 1075, FIG. 1.

S. Jallet et al, "Characterization of Recombinant Human Factor IX Expressed in Transgenic Mice and in Derived Trans–immortalized Hepatic Cell Lines," Embase Databank, Abstract No. 90288437; see abstract and Embo J. 1990, 9/10 3295–3301.

Choo et al (1987) Nucleic Acids Res. 15, 871–884.
R. Brinster et al 1988) Proced. Natl. Acad Sci, 85, 836–840.
Ciliberto et al (1985) Cell 41, 531–540.
Anson et al (1984) The EMBO J. 3, 1053–1060.
Choo et al (1987) "Expression of Active Human Clotting Factor IX in Transgenic Mice", Nucl. Acids Res. 15, 871–884.
Ciliberto et al (1985) "Cell Specific Expression of a Transfected Human $\beta_1$–antitrypsin Gene", Cell 41, 531–540.
Anson et al (1984) "The Gene Structure of Human Anti–Haemophilic Factor IX", EMBO J. 3, 1053–1060.

*Primary Examiner*—Deborah Crouch
*Attorney, Agent, or Firm*—Burns, Doane, Swecker & Mathis, L.L.P.

[57] ABSTRACT

Cell lines have been prepared from transgenic mice comprised of a first exogenous DNA sequence encoding human factor IX which is controlled by a promoter region specific for hepatic cells and a second exogenous DNA sequence encoding an oncogene, such as the SV40 virus gene encoding the T-antigen or the mouse c-myc gene, which is controlled by a promoter region specific for hepatic cells. Promoter regions specific for hepatic cells included the promoter region for the factor IX gene and the promoter region for the $\alpha$-1 antitrypsin gene. The cultured cells produce biologically active human factor IX which is then isolated from the culture media.

12 Claims, 9 Drawing Sheets

FIG_1

FIG_2

FIG_3

FIG_4

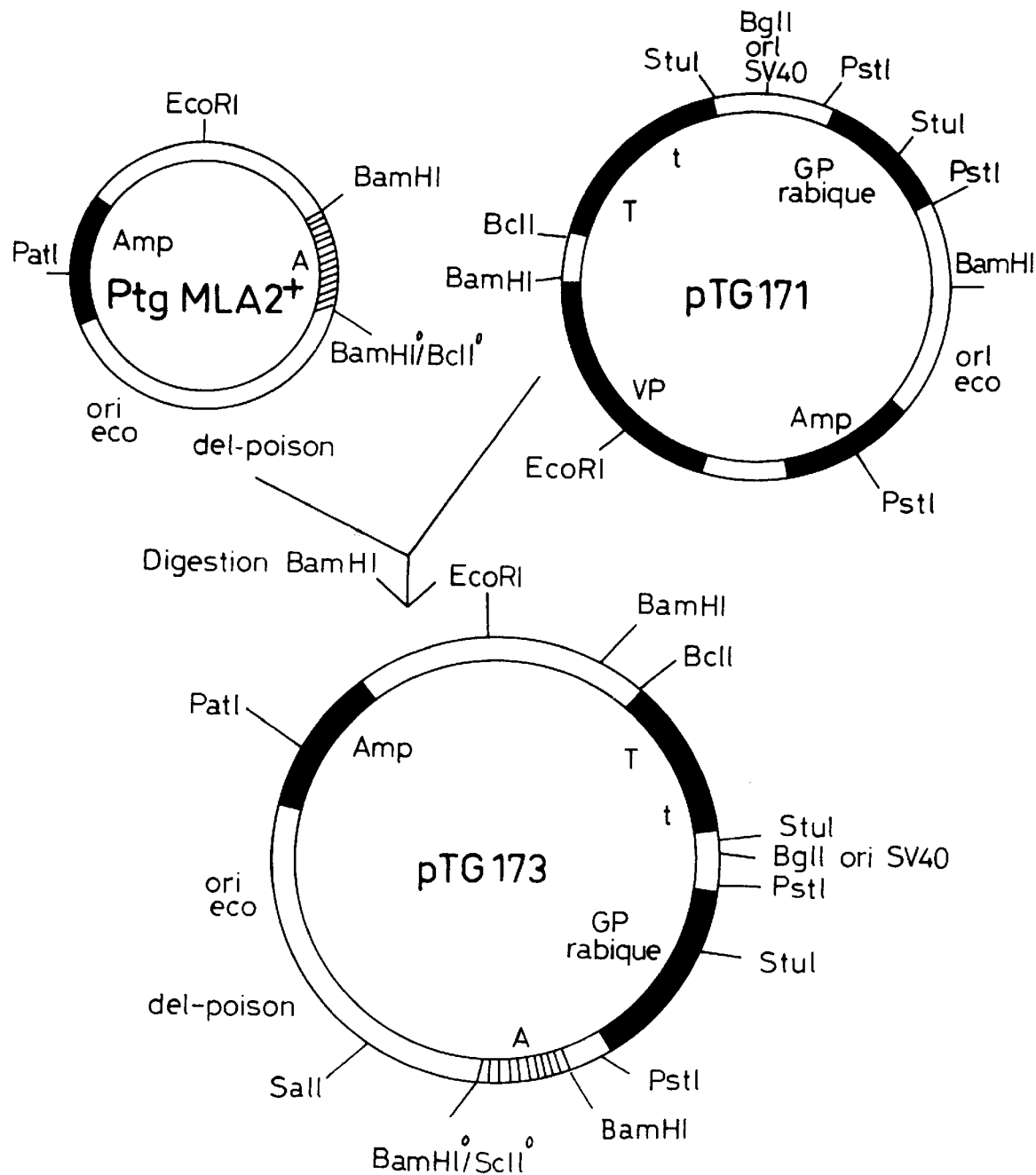
FIG_8a

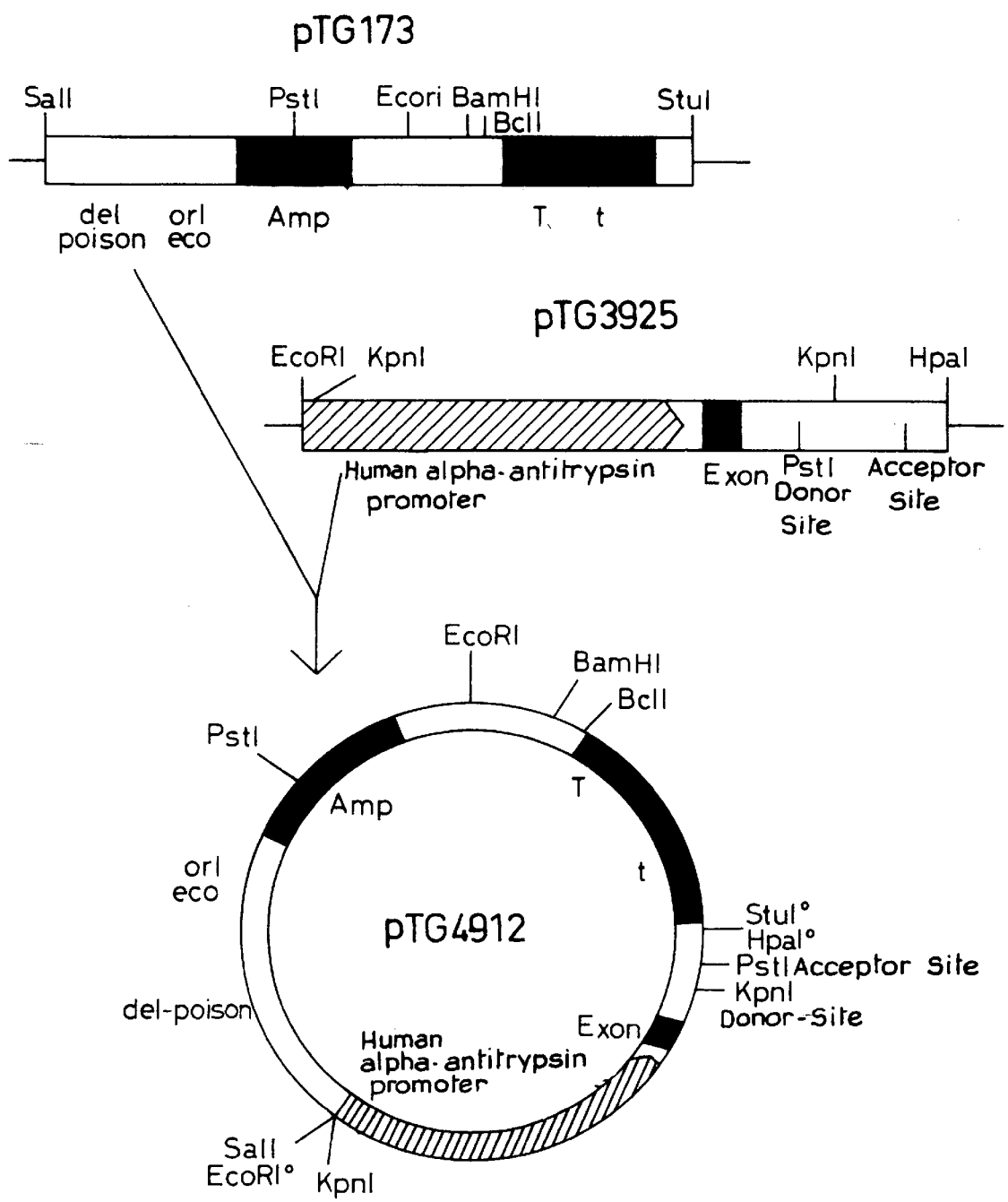
FIG_8b

CELL LINES FROM A TRANSGENIC MOUSE WHICH EXPRESS BIOLOGICALLY ACTIVE IX FACTOR

This application is a continuation of application Ser. No. 08/038,085, filed Mar. 29, 1993, abandoned, which is a continuation of application Ser. No. 07/675,889, filed as PCT/FR90/00606 Aug. 9, 1990, published as WO91/02056 Feb. 21, 1991, now abandoned.

The present invention relates to new immortalized cell lines obtained from transgenic animals, which express a biologically active factor IX, as well as to a new method for producing factor IX from the cell lines according to the invention.

Human factor IX is a protein of 415 amino acids (mature form), naturally present in the blood, which participates in the cascade of reactions leading to blood coagulation. Factor IX is chiefly synthesized in the liver, initially in the form of a precursor which is then subjected to at least four post-translational modifications: (i) a γ-carboxylation involving 12 glutamic acid residues, (ii) a glycosylation, (iii) a β-hydroxylation of the aspartic acid residue at position 64, and also (iv) the relinquishing by proteolytic cleavage of the signal peptide, followed by that of the propeptide. Factor IX thus processed is secreted into the blood. When a blood coagulation event takes place, the single-chain circulating form of factor IX (zymogen form) is cleaved in the presence of activated factor XI to give the double-chain activated form of factor IX (factor IXa), which then participates in a complex also comprising factor VIIIa, phospholipids originating from the membrane of blood platelets and calcium.

A hereditary deficiency of human factor IX is the cause of a serious disease, type B hemophilia, which affects one male subject in thirty thousand. At the present time, patients are treated by infusion of concentrated factor IX preparations derived from human plasma. The patients are thus subjected to not insignificant risks of infection as a result of the possible presence of pathogenic agents not detectable in the blood of the donors. In order to overcome this major drawback, research has been undertaken for a long time to produce factor IX by recombinant DNA techniques. Various expression systems have been proposed, in particular systems involving mammalian host cells. Nevertheless, it was soon found that the factor IX produced in this manner was not correctly processed, and that its activity was far lower than that of factor IX derived from blood plasma.

Concomitantly, expression of human factor IX in transgenic animals has also been obtained. Choo et al., Nucl. Acids Res. (1987) 15: 871 reports the expression of this protein in transgenic mice into which complementary DNA (cDNA) coding for factor IX, placed under the control of the inducible promoter of the sheep metallothionein Ia gene, had been introduced beforehand. From this promoter, a significant level of transcription is induced only in the presence of zinc. Although the factor IX thus produced is biologically active, the experiment of Choo et al., although of scientific interest, can hence not have an industrial application for obvious reasons of efficiency and on obvious ethical grounds.

It has now been found that immortalized cell lines derived from the liver of transgenic animals which have integrated in their genome one or more DNA fragments comprising a sequence coding for human factor IX can, when cultured, produce a factor IX whose activity is similar to that of factor IX present in human blood plasma.

Accordingly, the invention proposes a trans-immortalized cell line of hepatic origin, capable of expressing a factor IX of human origin whose activity is similar to that of factor IX present in human plasma, which has integrated in its genome an exogenous DNA fragment comprising a region coding for human factor IX; said sequence [sic] being placed under the control of a promoter region specific to the liver.

"Factor IX of human origin" is understood to mean any protein having the following two characteristics:

The protein is selected from human factor IX whose amino acid sequence is given in Anson et al., EMBO J. (1984) 3: 1053, and all analogs of the latter which have modifications in the amino acid sequence. These modifications can be deletions, insertions, or replacements of amino acids by others. "Human factor IX analog" is also understood to mean any protein having the same amino acid sequence as human factor IX, but having different post-translational modifications.

The protein has a coagulant activity as demonstrated by the kaolin coagulation test (one-stage assay) described by Austen & Rhymes (1975), A laboratory manual of blood coagulation, Blackwell Scientific Ed.; this activity is referred to in the text below as "factor IX" activity. As a guide, a detailed description of a particular procedure for this test is given below.

100 µl of a factor IX-deficient plasma (Stago) and 100 µl of a cephalin/kaolin solution [25 mg of kaolin (Merck; reference 1906); 100 µl of cephalin (Stago) for a final volume of 10 ml in Owren & Koller buffer (5.5 g/l of 5,5-diethylbarbituric acid, 3.69 g/l of sodium acetate, 0.63% NaCl, pH 7.3) [lacuna] are added to 100 µl of an aliquot of a sample to be tested. If necessary, this sample may be diluted beforehand in imidazole buffer (1.75 g/l; pH 7.4). This preparation is incubated for 180 seconds at 37° C. and 100 µl of 0.025M $CaCl_2$ are then added. The latency time before formation of a clot (coagulation time) is measured automatically (Behring Fibrintimer 10). The "factor IX" activity is thereafter established on the basis of a calibration series prepared as follows: A control plasma containing factor IX (Stago control plasma N FVIII-FIX, the activity of which is given by the supplier; 1 U=5 µg of factor IX) is diluted 10-, 20-, 40-, 80-and 160-fold in imidazole buffer. The coagulation time is measured for each of the dilutions and the calibration curve is drawn ("factor IX" Unit as a function of coagulation time on a logarithmic scale). When the procedure described above is carried out, a test sample is considered not to have "factor IX" activity if the measured activity is less than 250 ng/ml.

When this test is carried out with the plasma of a transgenic animal expressing human factor IX, a double series of samples should be used; the first series comprising plasma as drawn, and the second series comprising plasma treated with neutralizing anti-human factor IX antibodies, insofar as these antibodies do not exhibit a cross-reaction with the factor IX of the animals in question. By evaluating the difference between the results obtained in parallel, this enables the factor IX activity due specifically to human factor IX to be revealed. Finally, if necessary, the plasma of the transgenic animals is diluted to a greater extent with imidazole buffer.

"Factor IX of human origin having an activity similar to factor IX present in human plasma" is understood to mean a factor IX of human origin which is represented by a given sample whose factor IX activity, measured in µg/ml employing the Austen & Rhymes test described above, is equivalent to at least 75%, preferably at least 80% or still better at least 90%, of the total amount of factor IX in the sample, measured in µg/ml by an ELISA test. An ELISA kit specific for factor IX is commercially available from Diagnostica Stago, Asnièeres, France. On the basis of the definition in the present paragraph, factor IX present in human plasma has a factor IX activity of approximately 100%. Generally speaking, a factor IX meeting the criterion of activity stated above is designated by the term "biologically active factor IX".

"Promoter region specific to the liver" is understood to mean a mammalian promoter, or part of the latter, capable of initiating the transcription of a coding sequence in a restricted number of mammalian cell types (not in all types), especially in a liver cell or cell of hepatic origin. Preferably, a promoter specific to the liver is a promoter capable of initiating the transcription of a coding sequence chiefly in a liver cell or cell of hepatic origin; for example, the α-antitrypsin or factor IX gene promoter. For the purposes of the present invention, the latter promoter is most especially preferred, although it has been assumed until now that expression controlled by the factor IX gene promoter is weaker than expression controlled by the α-antitrypsin gene promoter.

Considered in very general terms, a cell line according to the invention may be obtained by an in vivo trans-immortalization process. It may hence be selected from a culture of liver tumor cells taken from a transgenic animal or from an animal in which a liver tumor originating from a transgenic animal has been propagated.

In the context of the present invention, "transgenic animal" is understood to mean an animal which possesses, integrated in its genome, an exogenous DNA fragment comprising a region coding for a factor IX of human origin or a region coding for an oncogene and which is capable of expressing the corresponding proteins. This transgenic animal can be a complete transgenic (all its cells possess the exogenous DNA fragment) or alternatively a mosaic (the exogenous DNA fragment occurs in a certain percentage of cells, but not in all). This transgenic animal is preferably a non-human mammal, more especially a murine and most preferably a mouse.

Taking into account the foregoing, a transgenic animal from which a cell line can be derived has to be doubly transgenic: for factor IX and for an oncogene.

According to a first embodiment, such an animal is obtained by the development of an egg which has been injected with, together, (i) a first exogenous DNA fragment comprising a region coding for factor IX and placed under the control of a promoter region specific to the liver, and (ii) a second DNA fragment comprising a region coding for an oncogene (oncogene sequence) placed under the control of a suitable promoter region, for example a promoter specific to the liver. The first and second DNA fragments may be injected as two different DNA molecules or alternatively as a single DNA entity.

According to a second, alternative embodiment, a transgenic animal for factor IX, capable of developing liver tumors from which cell lines according to the invention may be established, may be obtained as follows: A DNA fragment comprising an oncogene region is injected into eggs in order to obtain a first animal which is transgenic for an oncogene. Concomitantly, a DNA fragment comprising a region coding for factor IX is injected in order to obtain a second transgenic animal. The first and the second transgenic animal are then crossed in order to obtain an offspring which is doubly transgenic for the oncogene and factor IX.

Accordingly, the invention also relates to:
 (i) a singly transgenic animal whose blood plasma contains a factor IX of human origin whose activity is similar to that of factor IX present in human blood plasma, which has integrated in its genome an exogenous DNA fragment comprising a region coding for a factor IX of human origin; said region being placed under the control of a promoter region specific to the liver; and
 (ii) a transgenic animal as described in (i), which is, in addition, capable of developing a liver tumor, since it has integrated in its genome an exogenous DNA fragment comprising a region coding for an oncogene placed under the control of a suitable promoter region, for example a eukaryotic promoter region or one of viral origin. Preferably, it is a promoter region specific to the liver.

Generally speaking, the oncogene can be any oncogene capable of inducing a liver tumor in the animal under consideration. For example, it can be the T antigen of the SV40 virus or the antigen encoded by the mouse c-myc gene.

For the purposes of the present invention, a DNA fragment comprising a region coding for human factor IX may be constructed in the form of an expression block, more specifically by placing said region under the control of a promoter region at the 5' end of the coding region, which can be a promoter specific to the liver or at least a portion of such a promoter sufficient to permit the expression of factor IX in a liver cell. Apart from a promoter region and a coding region, the expression block can also comprise transcription termination stop elements.

The sequence of the region coding for factor IX can be:
 of the genomic type; for example, in the case of human factor IX, it is, in particular, the sequence described in Anson et al. (supra), which comprises 8 exons (exons A to H) and 7 introns (introns 1 to 7), or a sequence corresponding to the sequence referred to above in which the size of at least one intron has been reduced by introducing a deletion.
 of the complementary DNA type; for example, in the case of human factor IX, it is the sequence described in Anson et al. (supra), bereft of the 7 introns.
 of the "mixed" type (also known as a minigene); for example, in the case of human factor IX, it is the sequence described by Anson et al. (supra) in which at least one of the 7 introns has been eliminated and in which at least one of the 7 introns has been retained. Preferably, only the first intron or part of the first intron is retained.

According to a preferred embodiment of the invention, it is chosen to employ a sequence of the genomic type.

The exogenous DNA fragment can, in addition, comprise an amplification region, such as a region coding for adenosine deaminase (ADA), which confers a progressive resistance to some antibiotics. The amplification region and the region coding for factor IX must be placed under the control of a common promoter region. By selection based on resistance to high doses of antibiotic, a cell line hyperproductive of factor IX could thereby be obtained.

This exogenous DNA fragment is initially constructed as a fragment inserted into an expression vector, for example a plasmid. Nevertheless, for use in the present invention, it must be put into linear form and dissociated from the other plasmid elements.

Moreover, the invention also proposes a method for preparing a cell line according to the invention, in which
 the tumorous liver (or liver undergoing tumorigenesis) of a transgenic animal according to the invention, or the tumorous liver of an animal in which tumorous liver cells derived from a transgenic animal according to the invention have been propagated, is removed, and said cell line is selected by culturing the cells of said liver.

Finally, the invention also relates to a method for preparing a factor IX of human origin having an activity similar to that of factor IX present in human plasma, in which a cell line according to the invention is cultured and said factor IX in the culture medium is subsequently harvested.

The invention is illustrated below and relates to the following figures:

FIGS. 8a and 8b show diagrammatically the construction of plasmid pTG4912.

EXAMPLE 1

Preparation of Vectors Carrying a DNA Fragment Comprising a Region Coding for Human Factor IX A. Cloning of a region coding for human factor IX A library of genomic DNA originating from a human lymphoblastoid cell line GM1202A (4XY) is produced in the bacteriophage λEMBL3 [Pavirani A et al., Bio\Technology (1987) 5: 389], and is then screened using the following synthetic oligonucleotide probes (21-, 22-and 25-mer):

5' AAGTACAAGCTGAGCTGTATT 3' [1] SEQ ID NO: 1
5' TGCCATGATCATGTTCACGCG 3' [2] SEQ ID NO: 2
5' CTCAGTACAGGAGCAAACCACCTTG 3' [3] SEQ ID NO: 3
5' TAGAATTTACATAGTCCACATCAGG 3' [4] SEQ ID NO: 4
5' GTCTCTACTAGCTGTAGATTGC 3' [5] SEQ ID NO: 5
5' GATTATAGGCGTGAGCCACTG 3' [6] SEQ ID NO: 6

Figure 1:
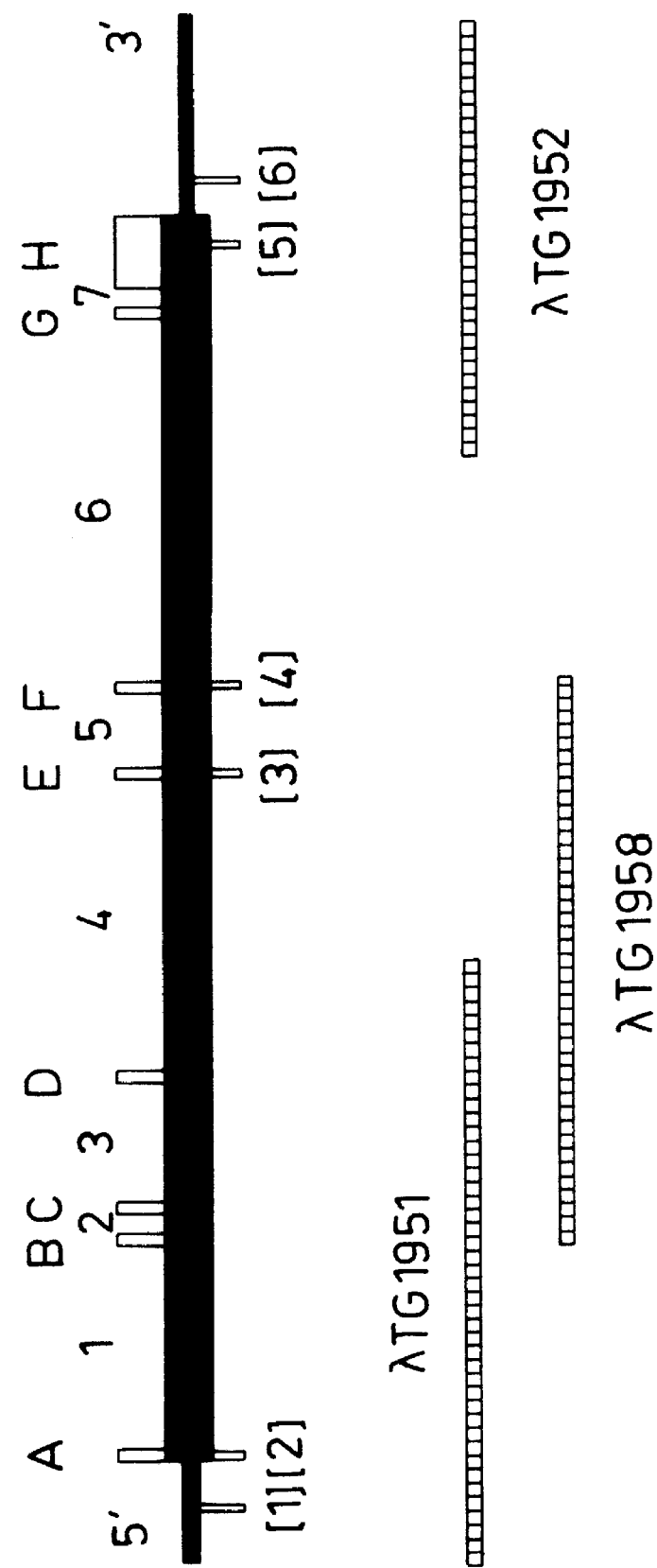
FIG. 1 shows diagrammatically the structure of the gene coding for human factor IX; the following are indicated: the position of the exons (A to H), the localization of the sequences recognized by the oligonucleotides used for screening the genomic library ([1] to [6]), and the pieces of DNA cloned into three lambda vectors, λTG1951, λTG1958 and λTG1952.

These correspond to different regions of the factor IX gene, as indicated in FIG. 1.

Three independent λ clones are identified using the probes, by Southern blotting: λTG1951, λTG1958 and λTG1952 (FIG. 1). The λTG1951 insert comprises the 5 kb of the promoter region and the region covering the first four exons of the gene. The λTG1952 insert comprises 2.3 kb of intron 6, intron 7, exons G and H and 10 kb of the adjacent sequence downstream of the polyadenylation signal. The λTG1958 insert extends from exon B to 0.47 kb downstream of exon F (it overlaps the λTG1951 insert by 7 kb). In conclusion, the three inserts described above collectively cover a large part of the gene, especially the eight exons and the adjacent 5' (5 kb) and 3' (10 kb) regions; only a region of intron 6 (6.7 kb) does not occur therein.

Figure 2:
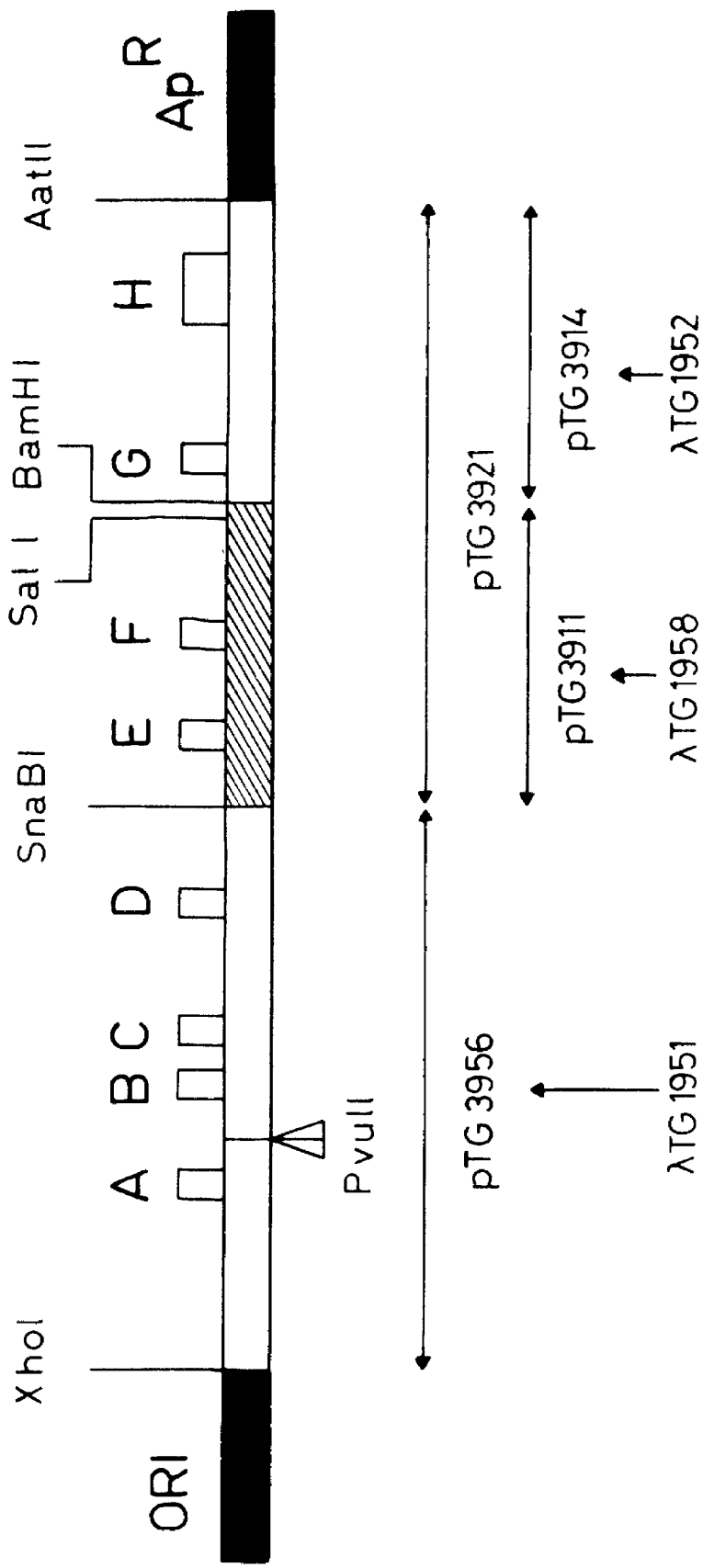
FIG. 2 shows diagrammatically the structure of plasmid pTG3960, specifying from which plasmids its fragments originate and from which lambda vector the latter have been constructed. The factor IX exons are designated by the letters A to H.

B. Construction of a plasmid containing a DNA sequence of the genomic type coding for human factor IX, placed under the control of the human factor IX gene promoter (pTG3960, FIG. 2).

The 15-kb SalI fragment of the clone λTG1958 is subcloned into the SalI restriction site of the vector ppolyIII-I* described in Lathe et al., Gene (1987) 57: 193, to give plasmid pTG3911.

A synthetic linker carrying single restriction sites (SfiI, EcoRI, KpnI, BamHI, XhoI and NotI) is introduced between the two EcoRI sites of cosmid pCV001 [Choo et al., Gene (1986) 46: 277], which are destroyed during the insertion, to generate plasmid pTG3909. The BamHI-EcoRI (4.3 kb) and EcoRI-EcoRI (1.8 kb) fragments isolated from the clone λTG1952 are cloned between the BamHI-EcoRI sites of pTG3909 to give pTG3914. The orientation of the EcoRI-EcoRI fragment is checked by enzymatic digestion. The 6.2-kb fragment (the above two fragments plus an EcoRI-AatII vector fragment) carrying the 3' portion of the factor IX gene (corresponding to exons G and H) is re-extracted from the cosmid by BamHI and AatII digestion. This fragment is then cloned between the same sites of pTG3911 to give plasmid pTG3921.

The SalI—SalI insert of λTG1951 is subcloned into the SalI site of plasmid pAT153 [Twigg A. J. and Sherrat D., Nature (1980) 283: 216] to give plasmid pTG3927. The central portion of intron 1 is removed by PvuII digestion followed by a ligation, to give plasmid pTG3952. This plasmid no longer has the two PvuII fragments (3.65 kb and 1.13 kb) internal to intron 1, but retains the PvuII fragment (4.38 kb) carrying exons B and C. The SalI—SalI insert of pTG3952 is passed on to the vector ppolyIII-I to give plasmid pTG3956, which has single sites at the 5' end. The XhoI-SnaBI fragment of pTG3956 is introduced between the XhoI-SnaBI sites of pTG3921 to give plasmid pTG3960 (FIG. 2), which contains:

5 kb of the factor IX gene promoter sequence,
22 kb of the fragment coding for factor IX (intron 1 is truncated in respect of these two PvuII fragments and intron 6 to the extent of 7.1 kb as a result of the further deletion of a 0.46-kb fragment due to the use of the BamHI site furthest downstream of the intron.
a few hundred base pairs of 3' genomic sequences downstream of the polyadenylation signal.

All the constructions are carried out by transfer to E. coli strain 5K, except for the final cloning step which employs E. coli strain BJ.

Figure 3:
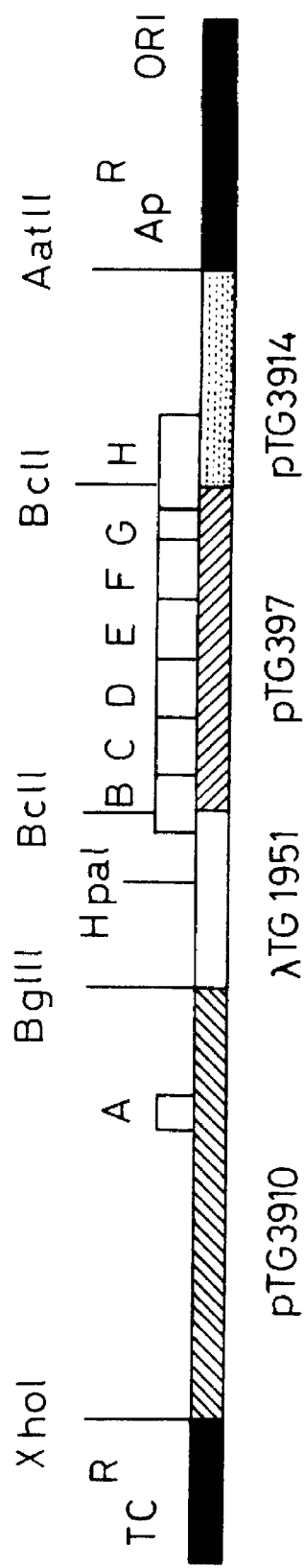
FIG. 3 shows diagrammatically the structure of plasmid pTG3954, specifying from which vectors its various fragments originate. The factor IX exons are designated by the letters A to H.

C. Construction of a plasmid containing a sequence of the "mixed" type coding for human factor IX, placed under the control of the human factor IX gene promoter (pTG3954, FIG. 3)

The 6.2-kb fragment containing the 3' end of the factor IX gene is re-extracted from cosmid pTG3914 by ClaI and AatII digestion. It is then cloned between the ClaI and AatII sites of the vector pAT153 to generate plasmid pTG3924. This construction is transferred to *E. coli* strain GM33 (dam). The genomic sequences included between the BclI and BglII sites are removed and replaced by a BClI-BglII fragment (2.34 kb) originating from phage λTG1951 and containing the 5' end of exon B and the 3' portion of intron 1, to give plasmid pTG3926. This cloning is performed in *E. coli* strain 5K. There remains 0.6 kb of genomic sequences originating from intron 6 between the BamHI and BglII sites which are removed during the final cloning step. Plasmid pTG3926 is transferred to *E. coli* strain GM33 (dam) so as to be able to re-form the portion of the complementary DNA between exons B and H by integrating the BclI fragment (1.4 kb) isolated from plasmid pTG397 described in European Patent Application EP-A-162,782 (this plasmid contains human factor IX complementary DNA), to give plasmid pTG3951.

The promoter portion, exon A and the remainder of intron 1 are isolated from plasmid pTG3910 (pTG3910 originates from cloning of the SalI fragment of λTG1951 into the vector ppolyIII-I*) in the form of an XhoI-BglII fragment. This fragment is integrated between these same sites in pTG3951 to give plasmid pTG3954 (FIG. 3), which hence contains a minigene for factor IX comprising the 5-kb portion of the promoter, exon A, the complete first intron, exons B to H in the form of a complementary DNA and a few hundred base pairs of the adjacent 3' portion downstream of the polyadenylation signal.

D. Construction of a plasmid containing a DNA sequence of the genomic type coding for human factor IX, placed under the control of the α-antitrypsin gene promoter (pTG3962, FIG. 4).

A KpnI-KpnI fragment containing the promoter region, the first non-coding exon and the 5' portion of intron 1 of the α-antitrypsin gene, the sequence of which is given by Long G. L. et al., Biochemistry (1984) 23: 4828 is inserted into the vector pUC18 [Yanisch-Perron C. et al., Gene (1985) 33: 103]. In particular, the 5' portion of intron 1 contains a splicing donor site.

A hybrid functional intron is then created by introducing into the XbaI site of the polylinker of pUC18 an adapter whose sequence is based on that of the 3' end of the first intron of the mouse c-myc gene. This synthetic fragment has the sequence: SEQ ID NO: 7.

GCATAACCCGGGCTAGCAG 3' SEQ ID NO: 8. This site is created two nucleotides upstream of the transcription initiation ATG. The HindIII insert thus modified is reintegrated in the vector ppolyIII-I* to give plasmid pTG3913.

The promoter portion and the beginning of the coding region of the α-antitrypsin gene, this region being equipped with the splicing acceptor site, are isolated from the vector pTG3925 in the form of an EcoRI-HpaI fragment. This fragment is integrated between the EcoRI and SmaI sites of plasmid pTG3913 to generate plasmid pTG3953. This insertion destroys the HpaI and SmaI cloning sites and is carried out in an exon region. The initiation ATG is provided by the region coding for factor IX (exon A). Sequencing of the fusion zone (between the synthetic sequence corresponding to murine c-myc and exon A) indicates that a nucleotide is lost during the cloning:

```
                        HpaI°SmaI°              (SEQ ID NO:9)
         ...CAGACAGCCACGACGGTTGGTTATG...
                  c-myc         factor IX
```

The 5' portion of the region coding for factor IX, containing the truncated intron 1 of the factor IX gene, is re-formed so as to apply the same strategy as above for assembly of the complete coding region. To this end, the EcoRV-SalI fragment isolated from plasmid pTG3952 is cloned between the same sites of pTG3953 to give plasmid pTG3957.

Figure 4:
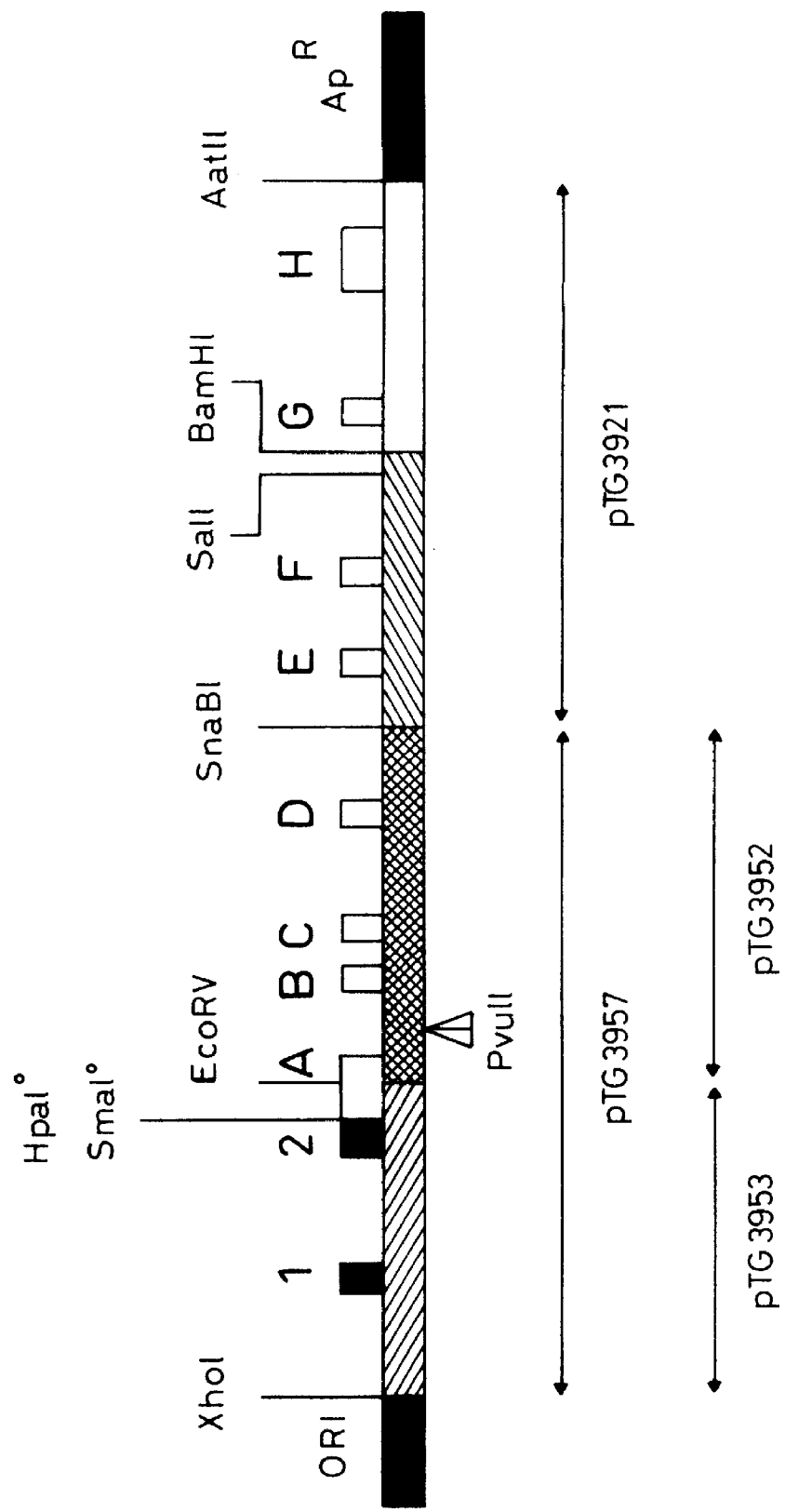
FIG. 4 shows diagrammatically the structure of plasmid pTG3962, specifying from which plasmids its various fragments originate. The factor IX exons are designated by the letters A to H (empty rectangles), the first non-coding exon of the α-antitrypsin gene by the FIG. 1 and the portion of the c-myc exon by the FIG. 2 (black rectangles).

Finally, the XhoI-SnaBI fragment (9.9 kb) of pTG3957 is transferred between the same sites of pTG3921 to give plasmid pTG3962 (FIG. 4). This final cloning step is carried out by transfer to *E. coli* strain BJ, whereas the previous steps are carried out by transfer to *E. coli* strain 5K.

In pTG3962 (FIG. 4), the first non-coding exon of the α-antitrypsin gene is retained.

EXAMPLE 2

Singly Transgenic Mice Expressing Human Factor IX

A. Production of transgenic mice pTG3954 is digested with SalI and SfiI while pTG3960 and pTG3962 are digested only with SfiI, so as to obtain in each case a DNA fragment comprising a block for the expression of factor IX dissociated from plasmid DNA fragments derived from pBR322. Each fragment thus released is purified on a sucrose gradient and injected into the male pronucleus of a fertilized egg of first-generation hybrid mice originating from crossing of a female C57/B16

```
       XbaI                              (*)                       HpaI    XbaI
5'TCTAGACTTGCTTCCCTTGCTGTGCCCCTCCAGCAGACAGCCACGACGGTTAACTCTAGA
       3' end of the first intron of 2nd c-myc
       the c-myc gene            exon
```

This synthetic fragment contains, from 5' to 3', an XbaI site, a splicing acceptor site (*) permitting correct splicing of the transcript (cleavage taking place between G and C), a cloning site at the blunt ends (HpaI) to permit fusion with the DNA fragment coding for factor IX at the exon regions, and finally an XbaI site. The orientation of this fragment is verified by sequencing. At the end of the construction, plasmid pTG3925 is obtained.

Concomitantly, a HindIII fragment (4 kb) of λTG1951 carrying the 5' portion of the promoter region of the factor IX gene, exon A and approximately 600 bp of intron 1 is subcloned into the vector M13TG130 [Kieny M. P. et al., Gene (1983) 26: 91]. An SmaI site (blunt ends) is then created by directed mutagenesis using the oligonucleotide 5' mouse with an SJL male according to the technique known to those skilled in the art. Each egg is then reimplanted in the uterus of a mouse for gestation to be continued.

The DNA of the tail tissues of the newborn is isolated so as to verify the integration of the exogenous DNA fragment in the genome of the animal by Dot-blot analysis using a suitable probe (BamHI—BamHI fragment of plasmid pTG397, described in European Patent Application EP-A-162,782) labeled with the isotype $^{32}$P, Blood is drawn from mice positive to the hybridization test, and the level of factor IX expression is determined in the serum by the ELISA method using the Diagnostica Stago assay kit (Asserachrom IX: Ag; Ref. 0410). The test is specific for human factor IX, and shows little or no cross-reaction with mouse factor IX.

The results are presented below.

TABLE 1

| Plasmid | Progenitrix No. | Sex | Factor IX expression (µg/ml) |
|---|---|---|---|
| pTG3960 | 1 | M | 6.97 |
| pTG3960 | 83 | F | 3.47 |
| pTG3962 | 18 | M | 1.82 |
| pTG3954 | 9 | M | 36.4 |
| pTG3954 | 58 | M | 8.02 |

Table 1 shows that the highest expression is obtained with the DNA fragments originating from pTG3954 and pTG3960, which contain the human factor IX gene promoter. In addition, to obtain a good level of expression, it is not necessary to have all of the introns (pTG3954).

Figure 5:
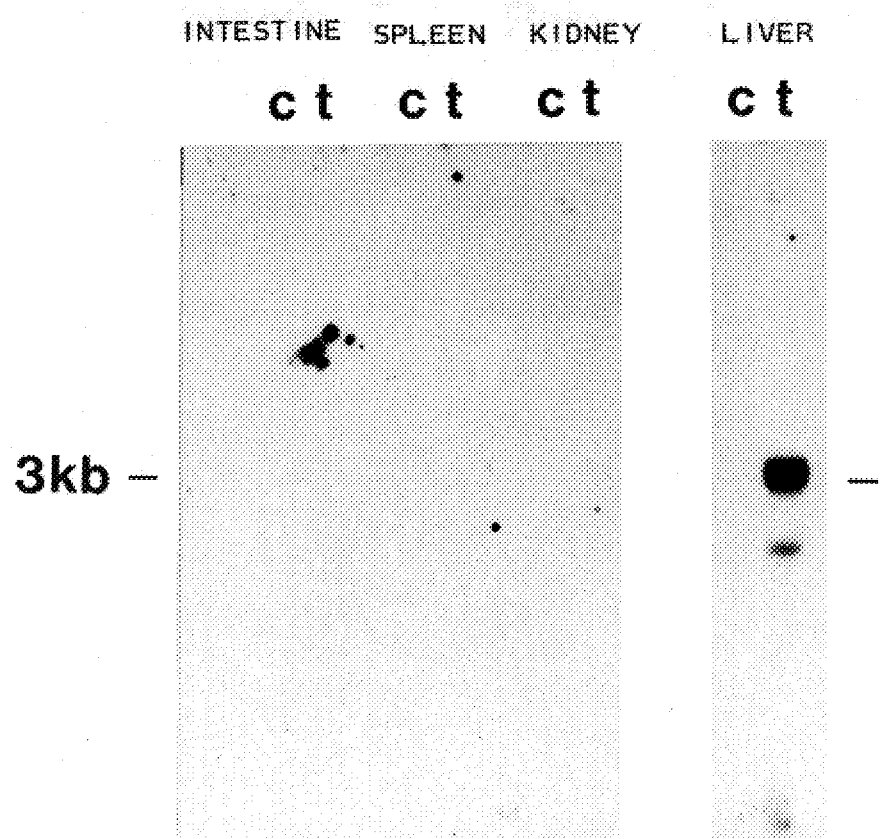
FIG. 5 shows the electrophoretic analysis of the RNAs prepared from different tissues of a transgenic mouse line expressing human factor IX ("C" for control mouse, and "T" for test).

B. Analysis of the mRNA Corresponding to Human Factor IX, Originating from Transgenic Mice The total RNA of several tissues (kidney, spleen, intestine and liver) is prepared from TMTG3960-1 line transgenic mice (factor IX promoter and genomic coding sequence). These RNAs are separated by electrophoresis on 1% agarose gel/formaldehyde, transferred onto a nylon membrane and hybridized with a radioactive human probe labeled with the isotope $^{32}P$ (900 bp of the untranslated 3' sequence of the factor IX gene which are cloned into ppolyIII-I*). FIG. 5 shows that human factor IX messenger RNAs (approximately 3 kb) are detected only in the hepatic tissues of TMTG3960-1 line transgenic mice, whereas no radioactive signal is detected with the RNAs isolated from tissues other than the liver, or in the liver of a control animal. Transgenic mice which express human factor IX specifically in the liver have hence been obtained.

Figure 6:
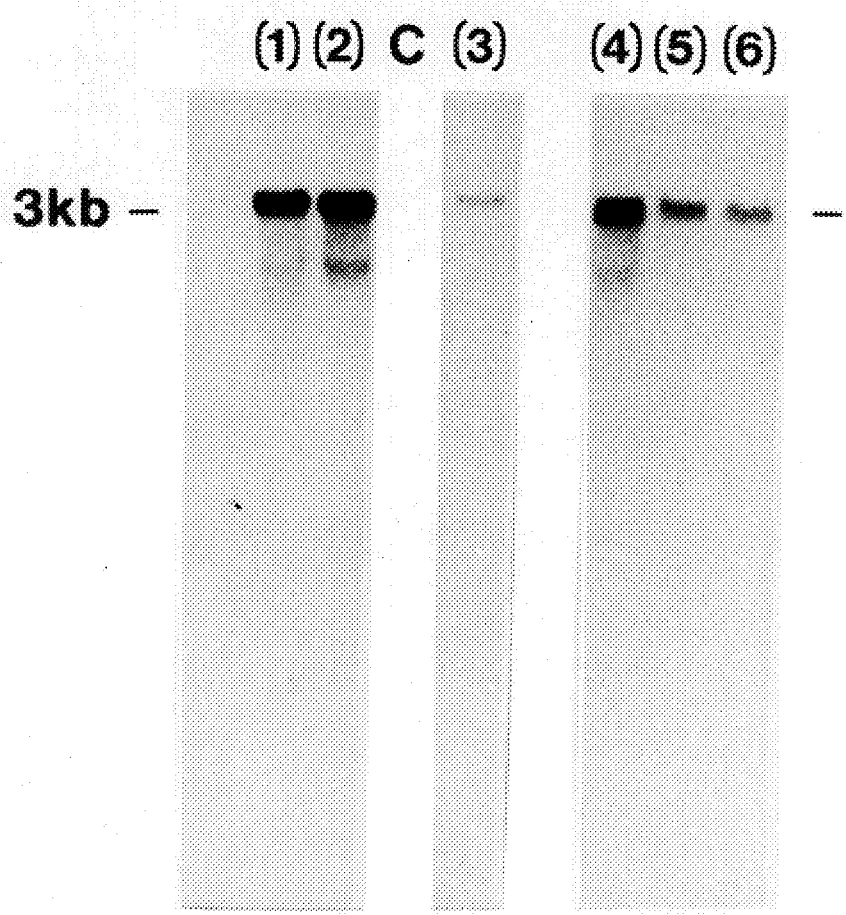
FIG. 6 shows the analysis of the messenger RNAs originating from the liver of transgenic mice expressing human factor IX; (1) and (2) TMTG3960-1 line mouse, "C" control mouse; (3) TMTG3962-18 line mouse; (4) TMTG3954-9 line mouse; and (5) and (6) TMTG3954-58 line mouse.

Moreover, when the messenger RNAs originating from the liver of all the transgenic mouse lines are analyzed with the same probe, the intensity of the signal is comparable overall to the level of expression (FIG. 6).

C. Analysis of Human Factor IX by Western Blotting

Figure 7:
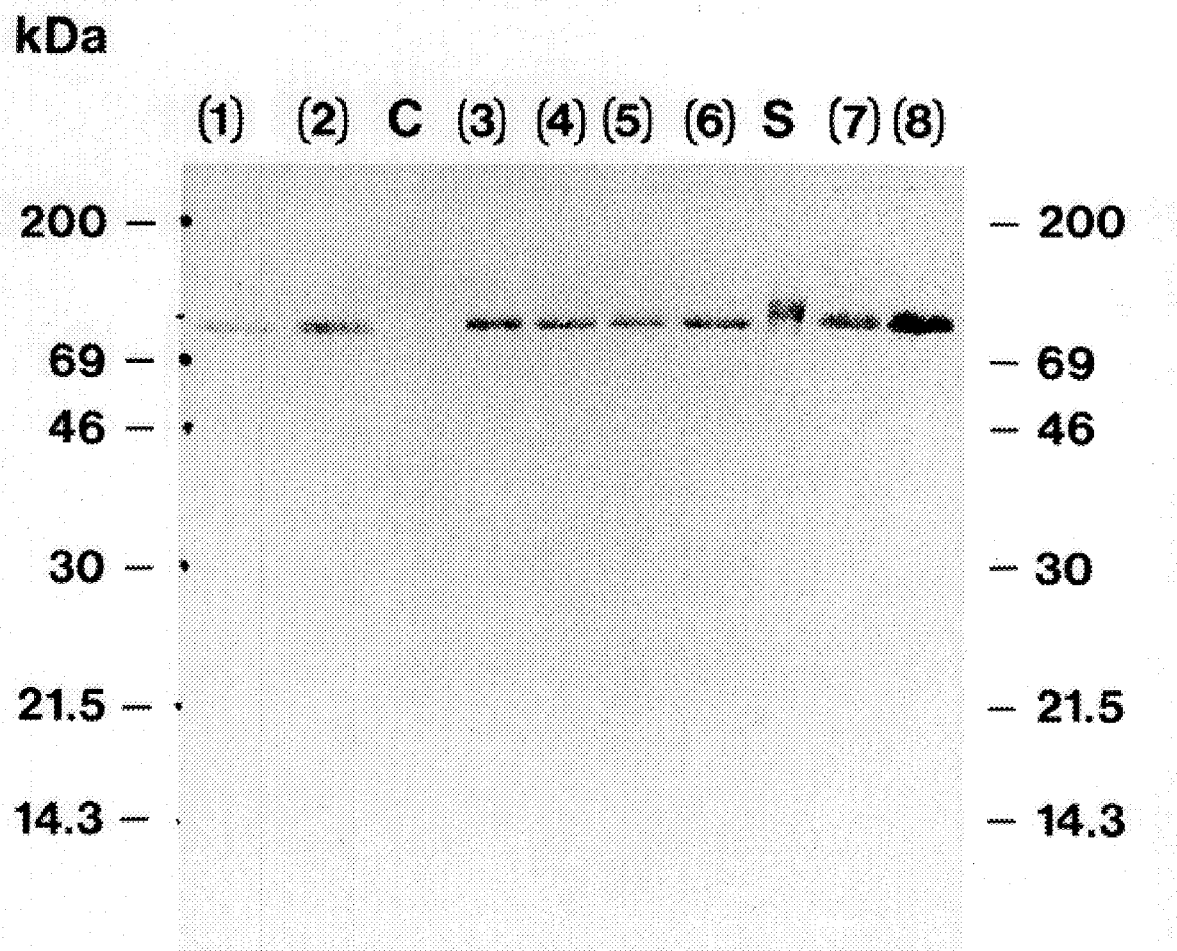
FIG. 7 shows the Western blot analysis of recombinant human factor IX isolated from the plasma of transgenic mice; (1) and (2) TMTG3954-58 line mouse; (C) control mouse, (3), (4), (5) and (6) TMTG3960-1 line mouse, "S" Stago factor IX and (7) and (8) TMTG3954-9 line mouse.

Plasma is drawn from transgenic mice originating from the lines TMTG3960-1, TMTG3954-9 and TMTG3954-58. A fraction is precipitated with barium and, after redissolution, analyzed by Western blotting. FIG. 7 shows that the human factor IX originating from a transgenic mouse has a molecular mass similar to that of factor IX of human plasma, thereby indicating that the product obtained is glycosylated (a feebly glycosylated or unglycosylated factor IX would have a lower molecular mass).

D. Coagulant Activity of the Human Factor IX Present in the Plasma of Transgenic Mice The concentration of the human factor IX in the plasma of mice of the various lines was determined by an ELISA test. The results are shown in Table 2. The various mice are identified by the line number (for example TMTG3960-1) followed by the generation (for example I for F1 generation), followed by a particular number. It may be noted that the concentration of human factor IX quantified in the first-generation TMTG3960-1 line mice is greater than that determined in the progenitrix mouse (see Table 1), since the latter is mosaic. On these same samples, the human factor IX activity is determined by a coagulation test by the one-stage assay technique of Austen and Rhymes, as reported above. The activity is determined in U/ml relative to a sample of human plasma used as a control (Stago 1 U/ml). Mouse plasma shows a considerable background (of the order of 1 U/ml). Preincubation of the samples of transgenic mouse plasma with a specific anti-human factor IX polyclonal antibody neutralizes this background and reduces the level of activity to that of mouse factor IX. The difference between the value obtained in the absence of antibody and that obtained in the presence of antibody corresponds to the activity due exclusively to human factor IX. This activity is recorded in µg/ml (1 U/ml=5 µg/ml of factor IX in normal human plasma taken as a reference). The results are presented in Table 2 below.

TABLE 2

| Mouse | Factor IX concentration (µg/ml) | Factor IX activity (µg/ml) | % |
|---|---|---|---|
| TMTG3960-1 I 3 | 25.5 | 22 | 86 |
| TMTG3960-1 I 29 | 22.5 | 21 | 93 |
| TMTG3960-1 I 46 | 29.2 | 22 | 75 |
| TMTG3962-18 II 9 | 2 | 2.3 | 116 |
| TMTG3962-18 II 8 | 3.9 | 4.4 | 113 |
| TMTG3954-58 I 24 | 9.6 | 7.3 | 76 |
| TMTG3954-9 II 16 | 19.8 | 19.8 | 100 |

Table 2 shows that, in the plasma of transgenic mice, human factor IX is biologically active, since the coagulant activity (measured in µg/ml) is equivalent to the quantity of factor IX measured by an ELISA test, this applying to all the lines.

E. Barium citrate precipitation test

The quality of the human factor IX present in the plasma of a transgenic mouse is also verified by a barium salt precipitation test [Bajaj S. P. et al., J. Biol. Chem. (1981) 256: 253]. γ-Carboxylated proteins are adsorbed and coprecipitate with barium citrate (insoluble salt), whereas proteins not so carboxylated remain in solution. The quantity of human factor IX (tot.) in the plasma of transgenic mice is determined before treatment. After treatment of the plasma with barium citrate, the adsorbed (ads), hence γ-carboxylated, fraction is redissolved and then quantified by an ELISA test. The quantities are referred to the volume of the sample and hence given in ng. The Ads/tot ratio, expressed as a percentage (%), quantifies the proportion of human factor IX which is γ-carboxylated.

TABLE 3

| Mouse | Total quantity of factor IX | Quantity of factor IX adsorbed | Ratio Ads/tot in % |
|---|---|---|---|
| TMTG3960-1 I 3 | 1429 | 981 | 69 |
| TMTG3960-1 I 46 | 1630 | 1104 | 67 |
| TMTG3960-1 III 6 | 573 | 504 | 88 |
| TMTG3962-18 II 9 | 152 | 152 | 100 |
| TMTG3962-18 II 8 | 103 | 102 | 99 |
| TMTG3954-58 I 24 | 370 | 343 | 93 |
| TMTG3954-9 II 16 | 356 | 440 | 82 |

Table 3 shows that the majority of the human factor IX present in mouse plasma is γ-carboxylated, since it is detected in the insoluble fraction. By comparison with factor IX present in human plasma, a degree of precipitation of 80 to 100% is obtained, depending on the experiment.

F. Purification and Characterization of the Factor IX Obtained from the Lines TMTG3960-1 and TMTG3954-9

The human factor IX obtained from mice originating from the lines TMTG3960-1 and TMTG3954-9 is purified by immunoaffinity chromatography. The eluted fraction is passed through reversed-phase HPLC to desalt the product, and N-terminal sequence determined by Edman degradation. The results obtained in each case indicate that the human factor IX present in the blood of the transgenic mice corresponds well to the mature form. No trace of human factor IX precursor is detected. The human factor IX of the transgenic mice is hence homogeneous and correctly processed.

EXAMPLE 3

Trans-immortalized Cell Lines Expressing Human Factor IX

A. Singly transgenic mice expressing an oncogene

The transgenic mouse line TMTG2984 expressing the c-myc oncogene is generated using the NotI—NotI fragment of plasmid pTG2984 described in Patent Application EP-A 0,298,807.

The transgenic mouse line TMTG4912 expressing the T and t tumor antigens of SV40 is generated using the SalI-EcoRI fragment of plasmid pTG4912 described below.

Plasmid pTG4912 is derived from plasmid pTG171 described in Patent EU 0,140,762 and plasmid pML2. Plasmid pML2 is derived from a "pJYM-like" plasmid described in the paper by Lusky M. et al. (Nature 293, (1981) pp. 79–81], in which the poison region of pBR322 which is deleted is a DNA fragment between nucleotides 1086 and 2457. The BamHI insert of SV40 is, in addition, deleted, and plasmid pML2 is thereby obtained.

The BamHI-BclI fragment 2553-2770 of the SV40 genome [Buchman et al. Tooze J. Eds., DNA Tumor Viruses—Second Edition Revised, pp. 799–841, (1981)] is inserted into the vector pML2 digested beforehand with BamHI, to give the vector pTGML2A$^+$ shown in FIG. 8.

The BamHI—BamHI fragment of plasmid pTG171 carrying the genes coding for the T and t antigens and for the rabies glycoprotein is inserted into the vector pTGML2A$^+$ digested beforehand with BamHI, to generate plasmid pTG173, shown in FIG. 8.

Plasmid pTG173 is digested with the enzymes StuI, which makes a blunt cut, and SalI, which leaves projecting 5' cohesive ends. The small StuI—StuI and StuI-SalI fragments are removed. The large SalI-StuI fragment containing the regions coding for the T and t antigens, the ampicillin resistance gene and the origin of replication is isolated and subjected to the action of Klenow polymerase (Amersham) in the presence of the 4 nucleotide triposphates (sic) ATP, GTP, CTP and TTP. The polymerase fills in the SalI site with the nucleotides and a DNA fragment having two blunt ends is thereby obtained.

Plasmid pTG3925 described above is digested with EcoRI, which leaves projecting 5' cohesive ends, and HpaI, which makes a blunt cut. The EcoRI-HpaI fragment containing the promoter, the first non-coding exon, a portion of the first intron carrying the splicing donor site of the α-antitrypsin gene and a synthetic splicing acceptor site is isolated and subjected to the action of "Mung Bean" nuclease (Biolabs), which cuts the cohesive ends of the EcoRI site. A fragment having two blunt ends is thereby obtained. This fragment is inserted into plasmid pTG173 digested with StuI and SalI, as prepared above, to obtain plasmid pTG4912 shown in FIG. 8.

B. Multi-transgenic Mice Expressing Human Factor IX and at Least One Oncogene

Doubly transgenic mice are generated by crossing TMTG3960-1 line mice with TMTG2984 line mice. The doubly transgenic state is verified by Dot-blot analysis with suitable probes. The progenitrix TMTG3960-1 X TMTG2984 line mice express both human α-antitrypsin and human factor IX. These two expression characters are transmitted to the offspring in Mendelian fashion. Three of these doubly transgenic mice develop liver tumors at the age of 12 months.

In order to obtain mice which develop tumors at an earlier age, a TMTG3960-1 X TMTG2984 line male is crossed with TMTG4912 line females. One of the triply transgenic offspring which are generated by this cross expresses 1 mg/ml of human α-antitrypsin and 40.3 μg/ml of human factor IX. This animal is sacrificed at the age of 6 weeks, and its liver (liver No. 1), which already shows hyperplasia, is removed. Another triply transgenic offspring which expresses 3 mg/ml of human α-antitrypsin and 60 αg/ml of human factor IX undergoes the same fate at the age of three months (liver No. 2).

C. Selection of Trans-immortalized Cell Lines

Each of the livers is treated as follows:

The tumorous hepatic tissue is dissociated by collagenase treatment as described by Howard & Pesh, J. Bio. Chem. (1968) 105: 3105, except for the perfusion step. Cells are then established in Williams' medium E (Gibco) supplemented with 10 ng/ml insulin, 300 ng/ml hydrocortisone, 10 μg/ml transferrin, 25 ng/ml epidermal growth factor (EGF), 2 mM glutamine, 50 U/ml streptomycin, 250 U/ml penicillin and 5% of dialyzed fetal calf serum (FCS). The addition of these various constituents is considered to be essential for the growth and maintenance of hepatocyte morphology. Primaria culture flasks (Falcon) are used for this first culture. Culturing is continued at 37° C. in a humidified atmosphere containing 10% of $CO_2$.

During this first culture, the cells are cultured in bulk form. Then, when they are at 80% confluence, they are detached in the presence of 0.05% trypsin and subcultured several times by successive passages in the supplemented medium described above. During the initial subculturings, the cells are transferred at the time of culturing (for approximately 10 min) to plastic flasks, to the walls of which the macrophages attach immediately and can thereby be removed. After 5 passages, FCS is replaced by 1 mg/ml bovine serum albumin (BSA). After 5 further passages, pure hepatocyte cultures are obtained, namely TMhep39 and TMhep48, selected from livers No. 1 and 2, respectively.

The quantity of factor IX produced by these cell lines is measured directly in the culture supernatant by an ELISA test. With TMhep39, the productivity is approximately 0.15 μg/$10^6$ cells/24 hours; and with TMhep48, it is between 0.29 and 0.55 μg/$10^6$ cells/24 hours. When the cultures are at a high cell density, production reaches 0.3–0.4 μg/ml/24 hours and approximately 0.7 μg/ml/24 hours, respectively.

The "factor IX" activity of the factor IX produced by the cell lines TMhep39 and TMhep48 is measured by the Austen & Rhymes test described above. In both cases, it is close to 100%.

The factor IX present in the culture supernatant of the two cell lines is purified on an immunoaffinity column. Sequencing of the N-terminal end confirms that the factor IX thereby produced corresponds well to the mature form. Western blotting likewise confirms that its electrophoretic mobility is identical to that of factor IX derived from human plasma.

D. Characterization of the Cell Lines TMhep39 and TMhep48

The production of albumin, which is a protein specifically secreted by the liver, is detected in the culture medium by an ELISA test using a rabbit anti-mouse albumin antiserum as the first antibody and a peroxidase-labeled rabbit anti-mouse albumin antibody as the second antibody. For both cell lines, the level of albumin secreted varies between 3 and 11 μg/ml/24 h.

In the TMhep39 line cells, the presence of messenger RNAs specific to liver cells is detected by the "spot-blot" technique described by Costanzi and Gillespie (1987) [in:

Berger S. L., Kimmel A. R. eds. Guide to Molecular Cloning Techniques, 152. Orlando: Academic press, 582–587.], using the total RNA prepared by the guanidium [sic] hydrochloride method as described by Chirgwin et al., Biochemistry (1979) 18: 701–710. Testing for mRNAs coding for mouse transferrin (1), mouse α-antitrypsin (2), mouse albumin (3), mouse β-actin (4), human α-antitrypsin (5), hamster vimentin (6), human factor IX (7), mouse c-myc (8), SV40 T antigen (9), glutathione S-transferase (10) and mouse α-fetoprotein (11) is initiated using probes whose sequences are, respectively, as follows:

AGTGGTCTCTGCTGACTCACAC 1 SEQ ID NO: 10
CTGTTTAGCAGGAACTTAGAGATGAGCTCC 2 SEQ ID NO: 11
TAGTGGGGTTGATAGGAAAGGT 3 SEQ ID NO: 12
GATGTCACGCACGATTTCCCTCTCA 4 SEQ ID NO: 13
GGTGATGATATCATGGGTGAGTTCATTTTC 5 SEQ ID NO: 14
TGCCGGTTCGAGGTGCCGGGG 6 SEQ ID NO: 15
CTCAGTACAGGAGCAAACCACCTTG 7 SEQ ID NO: 16
AGATATCCTCACTGGGCGCGGGCGG 8 SEQ ID NO: 17
AATAGCAGACACTCTATGCCTGTGTGGAGT 9 SEQ ID NO: 18
CTAAAGAGCGACCCAGGTGCCT 10 SEQ ID NO: 19
GGTGAGTTCTTGAGTATTCA 11 SEQ ID NO: 20

The probe corresponding to β-actin, a ubiquitous protein, is used as a positive control. The absence of hybridization is correctly observed when probe 6 (negative control) and probe 11 (corresponding to a protein exclusively expressed at foetal, that is to say undifferentiated, level) are used. A positive response is observed for albumin, human and mouse α-antitrypsins, glutathione transferase, human factor IX, mouse c-myc, SV40 T antigen and transferrin.

The results reported above indicate clearly that the cell lines obtained after successive subculturings retain a stable and differentiated phenotype.

*E. coli* strain BJ transformed by plasmid pTG3960 was deposited on Jul. 19, 1989, with the C.N.C.M. (National Collection of Microorganism Cultures), 25, rue du Dr. ROUX 75724 PARIS under number I-893.

The cell line TMhep48 was deposited on Aug. 9, 1990, with the C.N.C.M. 25, rue du Dr. ROUX 75724 PARIS under number I989.

We claim:

1. A transgenic mouse which develops a liver tumor, wherein the tumor produces biologically active human factor IX, said mouse having integrated into its genome:
(i) a first exogenous DNA sequence encoding human factor IX, wherein said DNA sequence is genomic DNA, and where expression of said DNA sequence is controlled by a promoter region specific for hepatic cells, wherein said promoter region is the factor IX gene promoter or a portion thereof sufficient to provide for expression of said DNA sequence; and
(ii) a second exogenous DNA sequence encoding an oncogene, wherein said oncogene is selected from the group consisting of the SV40 virus gene encoding T-antigen and the mouse c-myc gene, where expression of the said DNA sequence is controlled by a promoter region specific for hepatic cells,
wherein said promoter region is an α-1 antitrypsin gene promoter,
wherein a cell line comprising TMhepTG48 is established from said mouse.

2. A cell line established from hepatic tissue of a transgenic mouse according to claim 1, wherein said cell line expresses biologically active human factor IX, said cell line having integrated in its genome:
(i) a first exogenous DNA sequence encoding human factor IX, wherein said DNA sequence is genomic DNA, and where expression of said DNA sequence is controlled by a promoter region specific for hepatic cells, wherein said promoter region is the factor IX gene promoter or a portion thereof sufficient to provide for expression of said DNA sequence; and
(ii) a second exogenous DNA sequence encoding an oncogene, wherein said oncogene is selected from the group consisting of the SV40 virus gene encoding T-antigen and the mouse c-myc gene, where expression of the said DNA sequence is controlled by a promoter region specific for hepatic cells, and wherein said promoter region is an α-1 antitrypsin gene promoter,
wherein said cell line comprises TMhepTG48.

3. A method for preparing a biologically active human factor IX, in which a cell line according to claim 2 is cultured and said factor IX is harvested from the culture medium.

4. A cell line established from hepatic tissue of a transgenic mouse according to claim 2, wherein said cell line expresses biologically active human factor IX, said cell line having integrated into its genome:
(i) a first exogenous DNA sequence encoding human factor IX, wherein said DNA sequence is genomic DNA comprising at least one intron, and where expression of said DNA sequence is controlled by a promoter region specific for hepatic cells, wherein said promoter region is the factor IX gene promoter or a portion thereof sufficient to provide for expression of said DNA sequence; and
(ii) a second exogenous DNA sequence encoding an oncogene, wherein said oncogene is selected from the SV40 virus gene encoding T-antigen and the mouse c-myc gene, where expression of the said DNA sequence is controlled by a promoter region specific for hepatic cells, wherein said promoter region is an α-1 antitrypsin gene promoter,
wherein said cell line comprises TMhepTG48.

5. A cell line according to claim 2, wherein said first exogenous DNA sequence is a minigene.

6. A transgenic mouse according to claim 1, wherein said first exogenous DNA sequence is a minigene.

7. A method for preparing a cell line comprising removing the tumorous liver of a transgenic mouse according to claim 1, and culturing the cells of said liver to select a cell line, wherein said cell line produces biologically active human factor IX, said cell line having integrated into its genome:
(i) a first exogenous DNA sequence encoding human factor IX, wherein said DNA sequence is genomic DNA comprising at least one intron, and where expression of said DNA sequence is controlled by a promoter region specific for hepatic cells, wherein said promoter region is the factor IX gene promoter or a portion thereof sufficient to provide for expression of said DNA sequence; and
(ii) a second exogenous DNA sequence encoding an oncogene, wherein said oncogene is selected from the group consisting of the SV40 virus gene encoding T-antigen and the mouse c-myc gene, where expression of the said DNA sequence is controlled by a promoter region specific for hepatic cells, wherein said promoter region is an α-1 antitrypsin gene promoter,
wherein said cell line comprises TMhepTG48.

8. A transgenic mouse which has integrated into its genome:
(i) a first exogenous DNA sequence encoding human factor IX, wherein said DNA sequence is genomic DNA comprising at least one intron, and where expression of said DNA sequence is controlled by a promoter region specific for hepatic cells;

and (ii) a second exogenous DNA sequence encoding an oncogene, wherein said oncogene is selected from the group consisting of the SV40 virus gene encoding T-antigen and the mouse c-myc gene, where expression of the said DNA sequence is controlled by a promoter region specific for hepatic cells, wherein said mouse produces biologically active human factor IX.

9. A transgenic mouse of claim 8, wherein said first exogenous DNA sequence is a minigene.

10. A cell line established from hepatic tissue of a transgenic mouse according to claim 8, wherein said cell line expresses biologically active human factor IX.

11. A cell line according to claim 10, wherein said first exogenous DNA sequence is a minigene.

12. A method for preparing a biologically active human factor IX, in which a cell line according to claim 10 is cultured and said factor IX is harvested from the culture medium.

* * * * *

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

A A G T A C A A G C  T G A G C T G T A T  T        2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

T G C C A T G A T C  A T G T T C A C G C  G        2 1

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CTCAGTACAG GAGCAAACCA CCTTG 25

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

TAGAATTTAC ATAGTCCACA TCAGG 25

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTCTCTACTA GCTGTAGATT GC 22

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GATTATAGGC GTGAGCCACT G 21

(2) INFORMATION FOR SEQ ID NO:7:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCTAGACTTG CTTCCCTTGC TGTGCCCCCT CCAGCAGACA GCCACGACGG TTAACTCTAG 60
A 61

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GCATAACCCG GGCTAGCAG 19

( 2 ) INFORMATION FOR SEQ ID NO:9:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CAGACAGCCA CGACGGTTGG TTATG                                                      25

( 2 ) INFORMATION FOR SEQ ID NO:10:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGTGGTCTCT GCTGACTCAC AC                                                        22

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

CTGTTTAGCA GGAACTTAGA GATGAGCTCC                                     30

( 2 ) INFORMATION FOR SEQ ID NO:12:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TAGTGGGGTT GATAGGAAAG GT                                                        22

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

GATGTCACGC ACGATTTCCC TCTCA                                              25

( 2 ) INFORMATION FOR SEQ ID NO:14:

( i ) SEQUENCE CHARACTERISTICS:
        ( A ) LENGTH: 30 base pairs
        ( B ) TYPE: nucleic acid ( C ) STRANDEDNESS: single
( D ) TOPOLOGY: linear ( i i ) MOLECULE TYPE: DNA (genomic)

( x i ) SEQUENCE DESCRIPTION: SEQ ID NO:14:

GGTGATGATA TCATGGGTGA GTTCATTTTC  30

( 2 ) INFORMATION FOR SEQ ID NO:15:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:15:

TGCCGGTTCG AGGTGCCGGG G  21

( 2 ) INFORMATION FOR SEQ ID NO:16:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:16:

CTCAGTACAG GAGCAAACCA CCTTG  25

( 2 ) INFORMATION FOR SEQ ID NO:17:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:17:

AGATATCCTC ACTGGGCGCG GGCGG  25

( 2 ) INFORMATION FOR SEQ ID NO:18:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:18:

AATAGCAGAC ACTCTATGCC TGTGTGGAGT  30

( 2 ) INFORMATION FOR SEQ ID NO:19:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: DNA (genomic)

-continued (x i) SEQUENCE DESCRIPTION: SEQ ID NO:19:

CTAAAGAGCG ACCCAGGTGC CT								22

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GGTGAGTTCT TGAGTATTCA								20